(12) United States Patent
Stossel et al.

(10) Patent No.: US 7,094,897 B2
(45) Date of Patent: Aug. 22, 2006

(54) RHODIUM AND IRIDIUM COMPLEXES

(75) Inventors: Philipp Stossel, Frankfurt (DE); Hubert Spreitzer, Viernheim (DE); Heinrich Becker, Glashütten (DE)

(73) Assignee: Covion Organic Semiconductors GmbH, (DE)

(*) Notice: Subject to any disclaimer, the term of this patent is extended or adjusted under 35 U.S.C. 154(b) by 104 days.

(21) Appl. No.: 10/474,090

(22) PCT Filed: Apr. 3, 2002

(86) PCT No.: PCT/EP02/03704

§ 371 (c)(1),
(2), (4) Date: Feb. 19, 2004

(87) PCT Pub. No.: WO02/081488

PCT Pub. Date: Oct. 17, 2002

(65) Prior Publication Data

US 2004/0133004 A1    Jul. 8, 2004

(30) Foreign Application Priority Data

Apr. 5, 2001    (DE) .................................. 101 16 962

(51) Int. Cl.
*C07D 401/14* (2006.01)
*C07D 405/14* (2006.01)

(52) U.S. Cl. .................. 546/4; 544/64; 544/124; 544/225; 544/229; 546/2; 556/136; 428/917; 428/690

(58) Field of Classification Search ................ 428/690, 428/917; 546/2, 4; 544/64, 124, 225, 229; 556/136
See application file for complete search history.

(56) References Cited

U.S. PATENT DOCUMENTS 4,539,507 A    9/1985    VanSlyke et al.
5,151,629 A    9/1992    VanSlyke
5,576,460 A    11/1996    Buchwald et al.
5,621,131 A    4/1997    Kreuder et al.
6,821,645 B1 *  11/2004    Igarashi et al. ............. 428/690

FOREIGN PATENT DOCUMENTS

EP        0802173        10/1997
EP        0842208        5/2000
EP        0707020        8/2000
EP        1028136        8/2000
WO        WO-92/18552    10/1992
WO        WO-00/22026    4/2000

OTHER PUBLICATIONS

Lamansky. S., et al, "Synthesis and Characterization of Phosphorescent Cyclometalated Iridium Complexes," Inorg. Chem 40:1704-1711, XP-002196399, (2001).
Hong Zhi Xie, et al, "Reduction of Self-Quenching Effect in Organic Electrophosphorescence Emitting Devices via the Use of Sterically Hindered Spacers in Phosphorescence Molecules," Advanced Materials 13:1245-1248, XP-002196400 (2001).
Grushin, V. V., et al, "New, efficient electroluminescent materials based on organometallic Ir complexes," Chem. Commun. 2001:1494-1495, XP-002196401 (2001).
Lamansky, S., et al, "Molecularly doped polymer light emitting diodes utilizing phosphorescent Pt(II) and Ir(III) dopants," Organic Electronics 2:53-62, XP-002196402 (2001).

* cited by examiner

*Primary Examiner*—Charanjit S. Aulakh
(74) *Attorney, Agent, or Firm*—Connolly Bove Lodge & Hutz

(57) ABSTRACT

The present invention describes novel organometallic compounds which are phosphorescence emitters. Such compounds can be used as active components (=functional materials) in a series of different types of application which can be classed within the electronics industry in the broadest sense.

The compounds according to the invention are described by the formulae (I), (Ia), (II) and (IIa).

22 Claims, No Drawings

RHODIUM AND IRIDIUM COMPLEXES

Organometallic compounds, especially compounds of the $d^8$ metals, will find use as functional components in the near future as active components (=functional materials) in a series of different types of application which can be classed within the electronics industry in the broadest sense.

The organic electroluminescent devices based on organic components (for a general description of the construction, see U.S. Pat. No. 4,539,507 and U.S. Pat. No. 5,151,629) and their individual components, the organic light-emitting diodes (OLEDs), have already been introduced onto the market, as confirmed by the car radios having organic displays from Pioneer. Further products of this type will shortly be introduced. In spite of this, distinct improvements are still necessary here, in order that these displays provide real competition to the currently market-leading liquid crystal displays (LCDs) or to overtake these.

A development in this direction which has emerged in the last two years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4–6].

For theoretical reasons relating to the spin probability, up to four times the energy efficiency and performance efficiency are possible using organometallic compounds as phosphorescence emitters. Whether this new development will establish itself depends strongly upon whether corresponding device compositions can be found which can also utilize these advantages (triplet emission=phosphorescence compared to single emission=fluorescence) in OLEDs. The essential conditions for practical use are in particular a long operative lifetime, a high stability against thermal stress and a low use and operating voltage, in order to enable mobile applications.

In addition, there has to be efficient chemical access to the corresponding organometallic compounds. In this respect, organorhodium and -iridium compounds are of particular interest. Especially taking into account the cost of rhodium and of iridium, it is of decisive importance in the case of these metals that efficient access is made possible to corresponding derivatives.

In the literature, two designs of OLEDs have hitherto been described which have phosphorescence emitters as coloring components. The first type (type 1) typically has the following layer construction [M. E. Thompson et al., Proceedings of SPIE, 31. Jul.–2 Aug. 2000, San Diego, USA, Volume 4105, page 119–124]:

1. Carrier plate=substrate (typically glass or plastics films).
2. Transparent anode (typically indium-tin oxide, ITO).
3. Hole transport layer: particularly based on triarylamine derivatives.
4. Electron transport and emission layer: this layer consists of an electron transport material which has been doped with the phosphorescence emitter.
5. Electron transport layer: for the most part based on aluminum tris-8-hydroxyquinoxalinate ($AlQ_3$).
6. Cathode: metals, metal combinations or metal alloys having a low emission function are generally used here, for example Al—Li.

The second type (type 2) typically has the following layer construction [T. Tsutsui et al., Jpn. J. Appl. Physl., 1999, 38, L 1502–L 1504]:

1. Carrier plate=substrate (typically glass or plastics films).
2. Transparent anode (typically indium-tin oxide, ITO).
3. Hole transport layer: particularly based on triarylamine derivatives.
4. Matrix and emission layer: this layer consists of a matrix material typically based on triarylamine derivatives which has been doped with the phosphorescence emitter.
5. Electron transport/hole blocking layer: typically based on nitrogen heterocycles.
6. Electron transport layer: for the most part based on aluminum tris-8-hydroxyquinoxalinate ($AlQ_3$).
7. Cathode: metals, metal combinations or metal alloys having a low emission function are generally used here, for example Al.

It is also possible to emit the light from a thin transparent cathode. These devices are correspondingly (depending on the application) structured, contacted and finally also hermetically sealed, since the lifetime of such devices is generally drastically reduced in the presence of water and/or air.

The characteristics of the above-described OLEDs have two weak points:

Firstly, the phosphorescence emitters which are based on iridium complexes and have been described hitherto are not suitable for building red OLEDs, since none of the existing phosphorescence emitters emit in the red, i.e. at an emission wavelength of greater than 615 nm. Although orange phosphorescence emitters have been reported [M. E. Thompson et al., Proceedings of SPIE, 31 Jul.–2 Aug. 2000, San Diego, USA, Volume 4105, page 119–124], no report has been made of any which generate a saturated red tone.

Secondly, it is evident from the efficiency-brightness curves that the efficiency decreases sharply with rising brightness. This means that the high brightnesses required in practice can only be achieved via a high power consumption. However, high power consumptions require high battery outputs of portable devices (mobile phones, laptops, etc.). In addition, the high power consumption, which is to a large extent converted to heat, can lead to thermal damage of the display.

These deficiencies in the prior art result in the following objects. Firstly, there is a need to obtain, for example, red triplet emitters and, secondly, triplet emitters have to be provided which have linear efficiency-brightness curves even at high brightnesses.

5'-Mono-, 5',5"-di- and 5',5",5"'-tris-diarylamino-functionalized tris-orthometalated organorhodium and organoiridium compounds, compounds (I/Ia) or (II/IIa), which are the subject-matter of the present invention, will be central key building blocks for generating highly efficient triplet emitters. An appropriate diarylamino functionalization can be used to adjust decisive material properties such as the wavelength of phosphorescence emission, i.e. the color, the phosphorescence quantum yield and the redox and temperature stability of the emitters, to name only a few properties by way of example.

In addition, there is a need for covalent incorporation of these active, light-emitting centers into a multitude of polymers. In this case, starting from the structures specified (see Examples 13, 22, 23, 24), typical C—C bond-volume reactions (e.g. STILLE or SUZUKI coupling) are possible in order to either further functionalize these halogen-functionalized compounds or to use them as (co)monomers in the preparation of corresponding polymers.

The class of the 5'-mono-, 5',5"-di- and 5',5",5"'-tris-diarylamino-functionalized tris-orthometalated organorhodium and organoiridium compounds, compounds (I/Ia) or (II/IIa), is novel and has hitherto not been described in the literature, and their efficient preparation and availability as pure materials is of great significance for a series of electrooptical applications.

Surprisingly, it has now been found that the wavelength of phosphorescence emission, i.e. the "color" of the emitted light, can be precisely adjusted over a wide wavelength range (see Table 1).

In comparison to the unsubstituted parent compound, fac-tris[2-(2-pyridinyl-κN)phenyl-κC]-iridium(III) which exhibits phosphorescence in the green, the 5'''-tris-diarylamino-functionalized tris-orthometalated organoiridium compounds, according to Examples 1, 3, 4, 5, exhibit a bathochromically shifted phosphorescence emission. Within the series of the substituents N-carbazolyl, diphenylamino, N-(1-naphthyl)-N-phenylamino, bis(4-methoxphenyl)amino, the bathochromic shift of the phosphorescence maximum increases. Accordingly, for example, fac-tris[2-(2-pyridinyl-κN)(5-(N-bis(4-methoxyphenyl))phenyl)-κC]-iridium(III), according to Example 5, emits in the red (see Table 1).

TABLE 1

Influence of the 5'-substituents on absorption and phosphorescence

| Reference<br>Ir(2-PhPy)₃ | see<br>Example 1 | see<br>Example 3 |
|---|---|---|
| $\lambda_{max, absorption}$<br>377 nm | $\lambda_{max, absorption}$<br>385 nm | $\lambda_{max, absorption}$<br>418 nm |
| $\lambda_{max, emission}$<br>523 nm<br>Green | $\lambda_{max, emission}$<br>529 nm<br>Green | $\lambda_{max, emission}$<br>581 nm<br>Yellow |
| see Example 4 | | see Example 5 |
| $\lambda_{max, absorption}$<br>379 nm | | $\lambda_{max, absorption}$<br>422 nm |
| $\lambda_{max, emission}$<br>594 nm<br>Orange | | $\lambda_{max, emission}$<br>620 nm<br>Red |

$\lambda_{max, absorption}$: maximum of the longest wavelength absorption bands
$\lambda_{max, emission}$: maximum of the phosphorescence bands after excitation in the maximum of the longest wavelength absorption bands
Measurement conditions: solution in dichloromethane, concentration: $10^{-4}$–$10^{-5}$ M/hydrazine hydrate $10^{-3}$ M, T = 25° C.,
Reference, Ir(2-PhPy)₃: fac-tris[2-(2-pyridinyl-κN)phenyl-κC]-iridium(III), the unsubstituted parent compound Red phosphorescence emitters are of decisive importance especially for the production of full color displays, for which the primary colors RED-GREEN-BLUE have to be available.

The nearest prior art of transition metal-catalyzed diarylaminations of purely organic aryl chlorides, bromides, iodides are in particular the studies of J. F. Hartwig et al., S. L. Buchwald et al., and also of S. P. Nolan et al. Among the large number of publications on this reaction type, reference is made hereinbelow to a few selected studies.

Hartwig and Buchwald describe in particular nickel- and palladium-catalyzed amination reaction using phosphine ligands and a base [J. F. Hartwig et al.: J. Am. Chem. Soc. 2000, 122(19), 4618–4630; J. Org. Chem. 1999, 64(15); S. L. Buchwald et al.: J. Organomet. Chem. 1999, 576(1–2), 125–146; U.S. Pat. No. 5,576,460; see also EP 0 802 173 A1]. Typically, conversions of 70–98% are achieved in these reaction types. The purification of the crude products is problematic and is frequently effected by complicated chromatographic methods.

In addition to the above-described methods, nickel- and palladium-catalyzed diarylamination reactions on purely organic aryl halides, in particular aryl chlorides, using nitrogen-containing ligand systems and a base have been described. Useful nitrogen-containing ligand systems have proven to be imidazol-2-ylidenes and their protonated form, the imidazolium salts, but also amines [S. P. Nolan et al.: Org. Lett. 2000, 2(14), 2053–2055, Org. Lett. 1999, 1(8), 1307–1309]. In this case also, conversions of 70–95% are typically achieved on simple model substrates, and the purification of the crude products is effected by complicated chromatographic methods.

The transition metal-catalyzed diarylamination of aryl halides coordinatively bound to a metal center, i.e. of organometallic aryl halides, as described hereinbelow, is novel and has hitherto not been described in the literature.

It has been found that, surprisingly, the novel diarylamino-substituted organometallic compounds (I/Ia) or (II/IIa), according to scheme 1 and 2, are obtained starting from the 5'-mono-, 5',5"-di- and 5',5",5"'-trihalogen-substituted tris-orthometalated organorhodium and organoiridium compounds (III) and (IV) respectively [preparation according to the unpublished DE 10109027.7], i.e. starting from organometallic aryl halides, by the transition-metal catalyzed reaction with an organic diarylamine, in the presence of a phosphorus or nitrogen additive and a base, and also with suitable choice of the reaction parameters such as reaction temperature, reaction medium, concentration and reaction times, reproducibly in about 90–98% yield, without using chromatographic purification methods, optionally after recrystallization in purities of >99% by NMR or HPLC (see Example 1–4).

The above-described process is particularly notable for three properties:

Firstly, the transition metal-catalyzed selective 5'-mono-, 5',5"-di- and 5',5",5"'-tri-diarylamination of coordinatively bonded aryl halides, i.e. of organometallic aryl halides, is unexpected and unknown in this form.

Secondly, the high yield attained, which is reflected in the reproducibly very good yields of isolated product, is unexpected and unique for the diarylamination of coordinatively bonded aryl halides.

Thirdly, the resulting compounds are obtained in very good purities of >99% by NMR or HPLC without complicated chromatographic purification, optionally after recrystallization. It is essential for use in optoelectronic components, or for utilization as intermediates for the preparation of corresponding compounds.

As outlined above, the compounds according to the invention had not been described at the priority date of the present application and are therefore novel.

The present invention therefore provides compounds (I) and (II) according to scheme 1

Scheme 1:

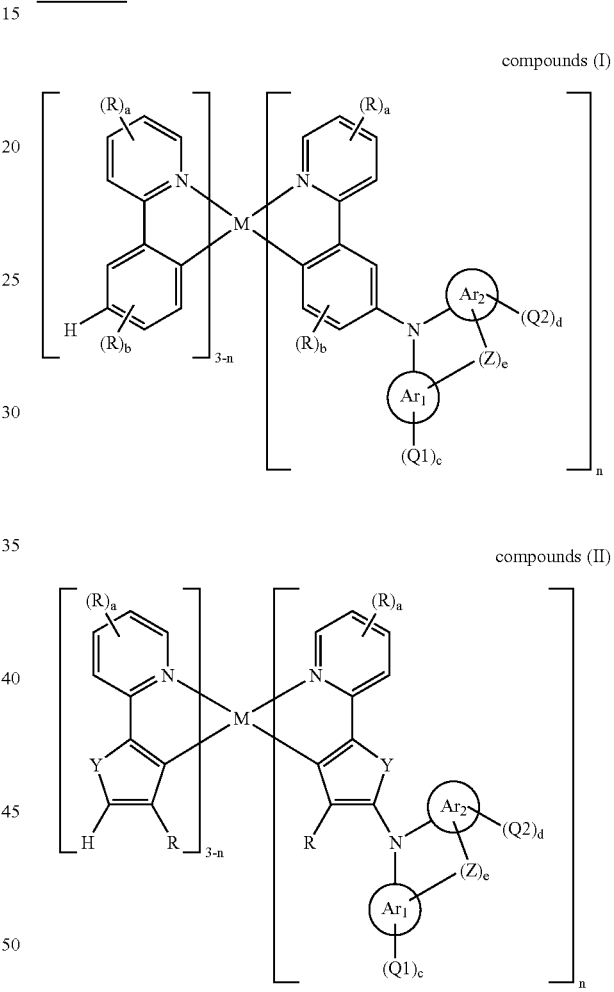

where the symbols and indices are defined as follows:

M is Rh, Ir;

Y is O, S, Se;

Z is B—$R^1$, $C(R)_2$, —CH=CH—, —$CR^1$=CH—, —$CR^1$=$CR^1$—, C=O, NH, $NR^1$, $PR^1$, $P(O)R^1$, $P(S)R^1$, O, S, S=O, $S(=O)_2$, Se or a C—C single bond;

R is the same or different at each occurrence and is H, F, Cl, $NO_2$, CN, a straight-chain or branched or cyclic alkyl or alkoxy group which has from 1 to 20 carbon atoms and in which one or more nonadjacent $CH_2$ groups may be replaced by —O—, —S—, —$NR^1$— or —$CONR^2$—, and in which one or more hydrogen atoms may be replaced by F, or an aryl or heteroaryl group having from 4 to 14 carbon atoms which may be substituted by one or more nonaromatic R radicals; and a plurality of R substituents, either on the same ring or on the two different rings together may in turn form a further mono- or polycyclic ring system;

$Ar_1$, $Ar_2$ are each an aryl or heteroaryl group having from 2 to 40 carbon atoms;

Q1, Q2 are the same or different at each occurrence and are each F, Cl, Br, CN, $NO_2$ or a straight-chain or branched or cyclic alkyl or alkoxy group which has from 1 to 20 carbon atoms and in which one or more nonadjacent $CH_2$ groups may be replaced by —O—, —S—, —CO—, —COO—, —O—CO—, —$NR^1$—, —$(NR^2R^3)^+A^-$ or —$CONR^4$, and in which one or more hydrogen atoms may be replaced by F, or an aryl or heteroaryl group having from 4 to 14 carbon atoms which may be substituted by one or more nonaromatic R radicals;

$A^-$ is a singly charged anion or its equivalent;

$R^1$, $R^2$, $R^3$, $R^4$ are the same or different and are each H or an aliphatic or aromatic hydrocarbon radical having from 1 to 20 carbon atoms;

a is 0, 1, 2, 3 or 4, preferably 0, 1 or 2, more preferably 0 or 1;

b is 0, 1, 2 or 3, preferably 0 or 1;

c, d are each 0, 1, 2, 3, 4 or 5, preferably 0, 1 or 2, more preferably 0 or 1;

e is 0 or 1;

n is 1, 2 or 3.

Although it is evident from the description, it is emphasized once more that, when e is 1 and Z is a C—C single bond, the two aryl radicals $Ar_1$ and $Ar_2$ are each bonded via a C—C single bond.

It is likewise emphasized that, when e is 0 for any desired Z, there is no bond between $Ar_1$ and $Ar_2$.

A further embodiment of the invention are those Rh and Ir complexes which at the same time have ligands of the type as in the case of compounds (I) and those of compounds (II), i.e. mixed ligand systems. These are described by the formulae (Ia) and (IIa), according to scheme 2:

Scheme 2:

compounds (Ia)

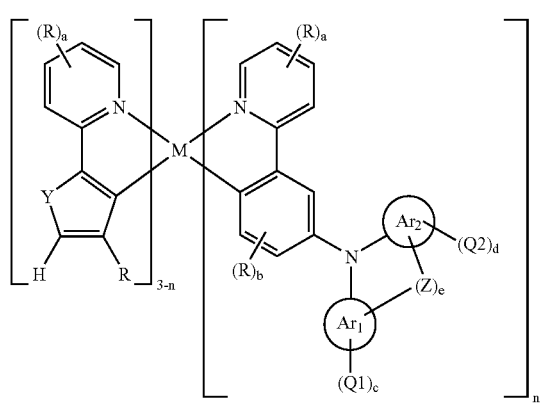

compounds (IIa)

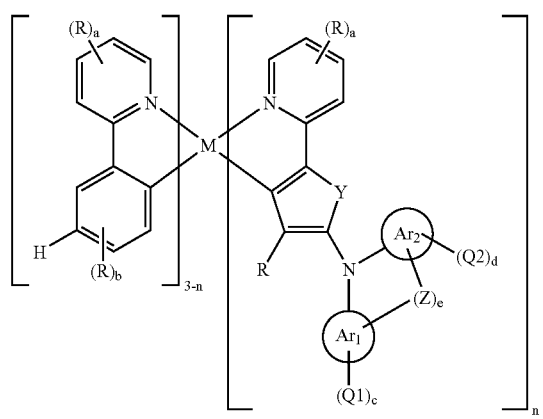

where the symbols and indices are as defined under the formulae (I) and (II).

Preference is given to compounds (Ia), (II) and (IIa) according to the invention in which the symbol Y=O, S.

Preference is likewise given to compounds (I), (Ia), (II) and (IIa) according to the invention in which the symbol Z=$C(R)_2$, —CH=CH—, —$CR^1$=CH—, —$CR^1$=$CR^1$—, C=O, NH, $NR^1$, O, S and C—C single bond.

Preference is likewise given to compounds (I), (Ia), (II) and (IIa) according to the invention in which the symbol R=H, F, Cl, $NO_2$, CN, a straight-chain or branched or cyclic alkyl or alkoxy group having from 1 to 6 carbon atoms.

Preference is likewise given to compounds (I), (Ia), (II) and (IIa) according to the invention in which the symbols $Ar_1$ and $Ar_2$ are the same or different at each occurrence and are each phenyl, 1- or 2-naphthyl, 1-, 2- or 9-anthracenyl, 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinolinyl, 2- or 3-pyrrolyl, 3-, 4-, 5-pyrazolyl, 2-, 4-, 5-imidazolyl, 2-, 3-thiophenyl, 2-, 3-selenophenyl, 2- or 3-furanyl and 2-(1,3,4-oxadiazol)yl.

Preference is likewise given to compounds (I), (Ia), (II) and (IIa) according to the invention in which the diarylamino unit $Ar_1$—N—$Ar_2$ is a diphenylamino, an N-(1-naphthyl)phenylamino, a di(1-naphthyl)amino, an N-(2-naphthyl)phenylamino, a di(2-naphthyl)amino, a bis(4-methoxyphenyl)amino, a bis(4-dimethylaminophenyl) amino, a carbazolyl, a 3,6-dichlorocarbazolyl, a 3,6-dibromocarbazolyl, a phenoxazine or a phenothiazine unit.

Preference is likewise given to compounds (I), (Ia), (II) and (IIa) according to the invention in which the symbols Q1 and Q2 are each H, F, Cl, Br, CN, $NO_2$ or a straight-chain or branched or cyclic alkyl or alkoxy group which has from 1 to 6 carbon atoms and in which one $CH_2$ group may be replaced by —$NR^1$—.

The compounds according to the invention can in principle be prepared by various processes, although the process described hereinbelow has proved to be particularly suitable.

The invention therefore further relates to a process for preparing the compounds (I) or (II) by reacting the compounds (III) and (IV)

compounds (III)

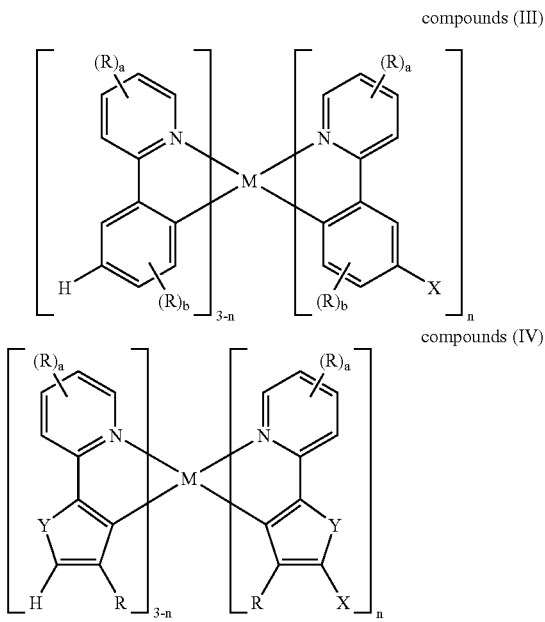

compounds (IV)

where
X is Cl, Br or I
and M, the R radicals and the indices a, b and n are each as defined under compound (I) or (II),
with a secondary diarylamine of the formula (I)

formula (I)

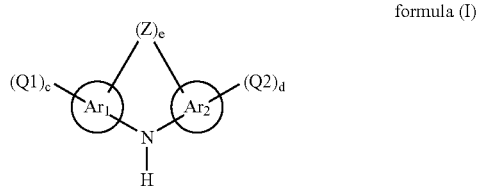

where the Z, $Ar_1$, $Ar_2$, Q1 and Q2 radicals and the indices c, d and e are each as defined under compounds (I) or (II), in a reaction medium and in the presence of a transition metal or of a transition metal compound, of a phosphorus or nitrogen additive and of a base.

Transition metals or transition metal compounds according to the invention are nickel or nickel compounds, or palladium or palladium compounds.

According to the invention, nickel or nickel compounds are, for example, elemental nickel, nickel sponge, nickel on kieselguhr, nickel on alumina, nickel on silica, nickel on carbon, nickel(II) acetate, nickel(II) acetylacetonate, nickel (II) chloride, bromide, iodide, addition compounds of $NiL_2X_2$ type where X is chlorine, bromine, iodine and L a neutral ligand, for example ammonia, acetonitrile, propionitrile, benzonitrile, or nickel(II) nitrate, nickel(II) sulfate, nickel(II) oxalate, biscyclooctadienenickel(0).

According to the invention, palladium or palladium compounds are, for example, elemental palladium, palladium sponge, palladium black, palladium on activated carbon, palladium on alumina, palladium on silica, palladium on alkali metal or alkaline earth metal carbonates such as sodium, potassium, calcium, strontium or barium carbonate, palladium on strontium sulfate or barium sulfate, or palladium compounds, for example palladium(II) acetate, palladium(II) trifluoroacetate, palladium(II) propionate, palladium(II) acetylacetonate, palladium(II) chloride, bromide, iodide, addition compounds of the $PdL_2X_2$ type where X is chlorine, bromine, iodine and L a neutral ligand, for example ammonia, acetonitrile, propionitrile, benzonitrile, cyclooctadiene, or palladium(II) nitrate, palladium(II) sulfate, tetraaminopalladium(II) acetate, tetrakis(acetonitrile)palladium(II) tetrafluoroborate, tetrakis(triphenylphosphino) palladium(0) and tris(dibenzylideneacetone)dipalladium(0).

The molar ratio according to the invention of nickel, of a nickel compound, palladium or of a palladium compound to the compounds (III) or (IV) is from 0.1n:1 to 0.00001n:1.

According to the invention, the phosphorus additive used is a phosphine.

Phosphine ligands according to the invention are selected from the group of triarylphosphines, diarylalkylphosphines, aryldialkylphosphines, trialkylphosphines, trihetarylphosphines, dihetarylalkylphosphines, hetaryldialkylphosphines, and the substituents on the phosphorus may be the same or different and chiral or achiral, and one or more of the substituents may link the phosphorus groups of a plurality of phosphines and some of these linkages may also be one or more metal atoms, for example tri-o-tolylphosphine, tri-mesitylphosphine, tri-o-anisylphosphine, tri-(2,4,6-trismethoxyphenyl)phosphine, tert-butyl-di-o-tolylphosphine, di-tert-butyl-o-tolylphosphine, dicyclohexyl-2-biphenylphosphine, di-tert-butyl-2-biphenylphosphine, triethylphosphine, triisopropylphosphine, tricyclohexylphosphine, tri-tert-butylphosphine, tri-tert-pentylphosphine, bis(di-tert-butylphosphino)methane, 1,1'-bis(di-tert-butylphosphino)ferrocene.

Particular preference is given to the phosphines dicyclohexyl-2-biphenylphosphine, di-tert-butyl-2-biphenylphosphine, tri-tert-butylphosphine, tri-tert-pentylphosphine.

According to the invention, the nitrogen additives used are imidazolium salts, imidazol-2-ylidenes or amines and amino carboxylic acids.

The nitrogen additives used are preferably imidazolium salts, for example 1,3-bis(phenyl)imidazolium hydrochloride, 1,3-bis(2-methylphenyl)imidazolium hydrochloride, 1,3-bis(2,6-dimethylphenyl)imidazolium hydrochloride, 1,3-bis(2,4,6-trimethylphenyl)imidazolium hydrochloride, 1,3-bis(2,6-di-isopropylphenyl)imidazolium hydrochloride, 1,3-bis(2,6-di-tert-butylphenyl)imidazolium hydrochloride, or imidazol-2-ylidenes, for example 1,3-bis(phenyl)imidazol-2-ylidene, 1,3-bis(2-methylphenyl)imidazol-2-ylidene, 1,3-bis(2,6-dimethylphenyl)imidazol-2-ylidene, 1,3-bis(2,4,6-trimethylphenyl)imidazol-2-ylidene, 1,3-bis(2,6-di-isopropylphenyl)imidazol-2-ylidene, 1,3-bis(2,6-di-tert-butylphenyl)imidazol-2-ylidene, or aromatic amines and amino carboxylic acids such as pyridine, lutidine, 2,2'-bipyridyl, or quinoline, or $\alpha,\beta,\gamma,\delta$-amino carboxylic acids or their N-alkylated forms or their sodium or potassium salts, for example anthranilic acid, dimethylanthranilic acid, 2-pyridinecarboxylic acid, dimethylglycine, dimethylaminobutyric acid or 3-indolylacetic acid.

The molar ratio according to the invention of the phosphorus or nitrogen additives in nickel, a nickel compound, palladium or a palladium compound is from 0.5:1 to 1000:1.

Bases according to the invention are organic bases, for example alkali metal and alkaline earth metal alkoxides, e.g.

lithium, sodium, potassium, magnesium, strontium and barium methoxide, ethoxide, propoxide, butoxide, isopropoxide, isobutoxide, sec-butoxide, tert-butoxide, phenoxide, organic amines, e.g. trimethylamine, triethylamine, tributylamine, diisopropylamine, N-ethyldiisopropylamine, morpholine, N-methylmorpholine, N-ethylmorpholine, pyridine, 2-, 3-, 4-methylpyridine, lutidine or collidine, tetraalkylammonium hydroxide, e.g. tetramethyl-, tetraethyl-, tetrapropyl- and tetrabutylammonium hydroxide, alkali metal and alkaline earth metal carboxylates, e.g. lithium, sodium, potassium, magnesium, strontium and barium formate, acetate, propionate, butyrate, oxalate or benzoate, or mixtures of the bases mentioned.

Bases likewise in accordance with the invention are inorganic bases, for example ammonia, alkali metal and alkaline earth metal oxides, e.g. lithium oxide, sodium oxide, potassium oxide, magnesium oxide, strontium oxide and barium oxide, alkali metal and alkaline earth metal hydroxides, e.g. lithium hydroxide, sodium hydroxide, potassium hydroxide, magnesium hydroxide, strontium hydroxide and barium hydroxide, alkali metal and alkaline earth metal carbonates, e.g. lithium carbonate, sodium carbonate, potassium carbonate, magnesium carbonate, strontium carbonate and barium carbonate, alkali metal hydrogencarbonates, e.g. lithium hydrogencarbonate, sodium hydrogencarbonate, potassium hydrogencarbonate, alkali metal phosphates, hydrogen phosphates, dihydrogen phosphates, e.g. lithium, sodium and potassium phosphate, hydrogen phosphate and dihydrogen phosphate, or mixtures of the bases mentioned.

The molar ratio according to the invention of the organic or inorganic base to the compounds (III) or (IV) is from 0.5 n:1 to 100 n:1.

Reaction media according to the invention are protic or aprotic, halogen-free or halogenated solvents, for example alcohols such as methanol, ethanol, propanol, butanol, polyhydric alcohols such as ethylene glycol or propylene glycol, nitriles such as acetonitrile, propionitrile or benzonitrile, ethers such as diethyl ether, THF or dioxane, aromatic hydrocarbons such as toluene, o-, m-, p-xylene, or a mixture of the isomeric xylenes, mesitylene, anisole, nitrobenzene or chlorobenzene, N,N-dialkylamides such as dimethylformamide, dimethylacetamide or N-methylpyrrolidinone, sulfoxides such as dimethyl sulfoxide, sulfones such as dimethylsulfone or sulfolane, halogenated hydrocarbons such as dichloromethane, trichloromethane, 1,1-dichloroethane, 1,2-dichloroethane, 1,1,2,2-tetrachloroethane.

According to the invention, the reaction is carried out within a temperature range from 0° C. to 200° C., preferably from 20° C. to 150° C., more preferably from 40° C. to 130° C.

According to the invention, the concentration of the rhodium or iridium reactants, compounds (III) or compounds (IV), is in the range from 0.0005 mol/l to 2 mol/l, more preferably in the range from 0.002 mol/l to 0.1 mol/l.

According to the invention, the rhodium or iridium reactants may be dissolved or suspended in the reaction medium.

According to the invention, the reaction is carried out within 1 hour up to 100 hours, preferably within from 1 h to 60 h.

According to the invention, the reaction can be carried out with the addition of inert ground media, for example ceramics, glass or metal spheres or Pall or Raschig rings.

The synthesis methods illustrated here can be used, inter alia, to prepare the examples of compounds (I) or (II) depicted hereinbelow.

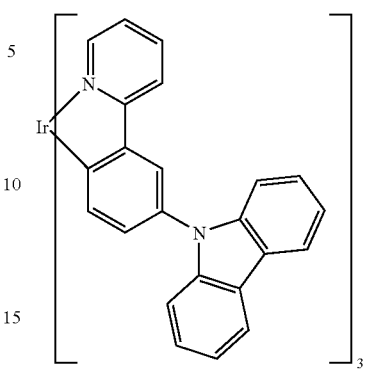

Example 1

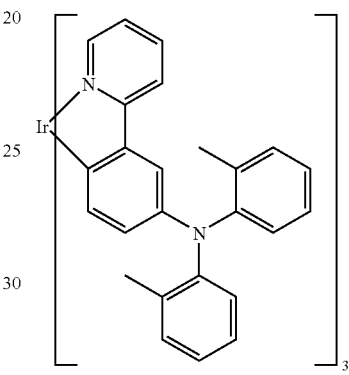

Example 2

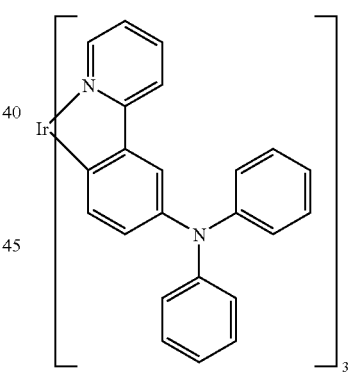

Example 3

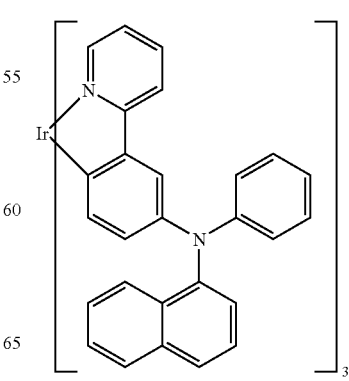

-continued
Example 4
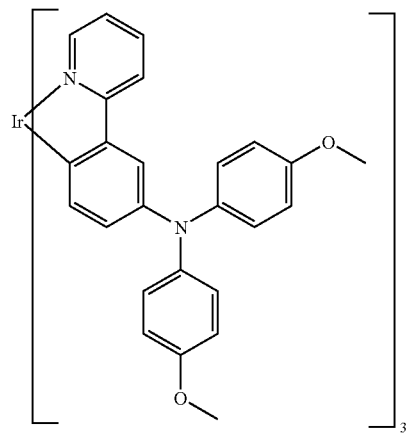
Example 5
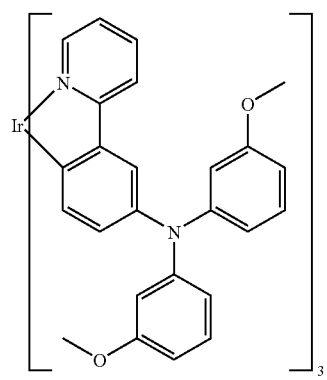
Example 6
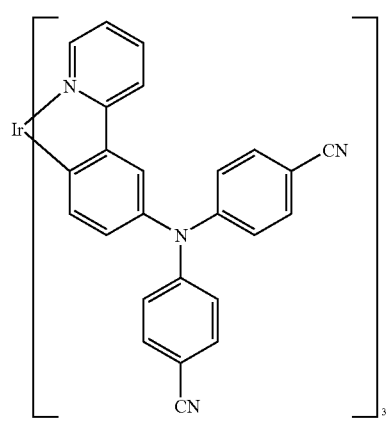
-continued
Example 7
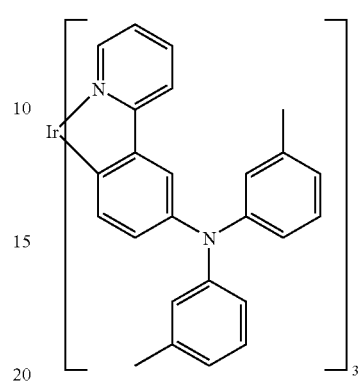
Example 8
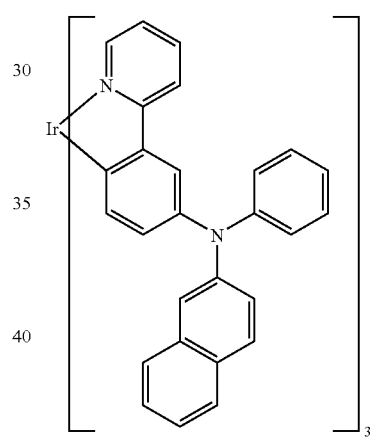
Example 9
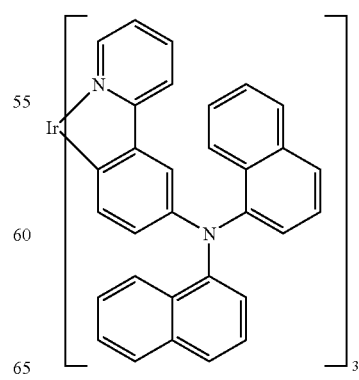

Example 10
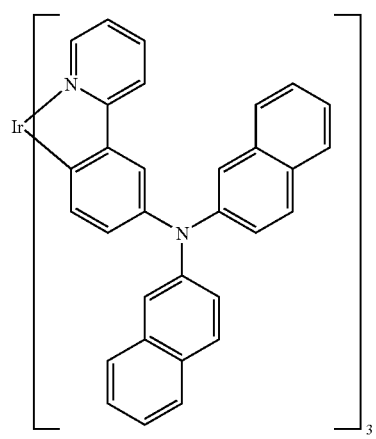
Example 11
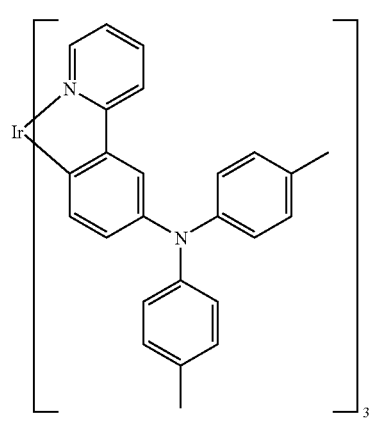
Example 12
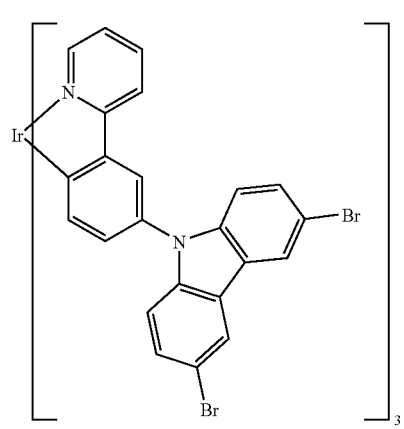
Example 13
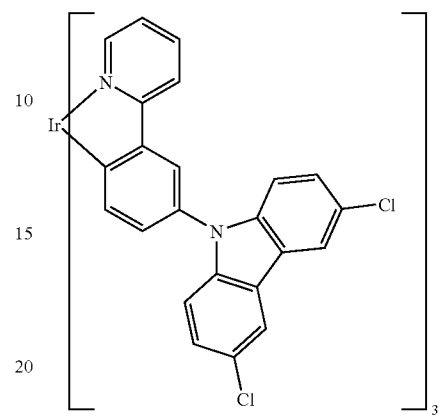
Example 14
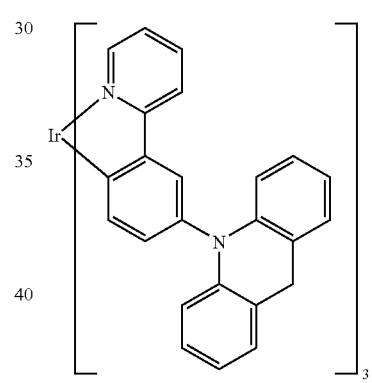
Example 15
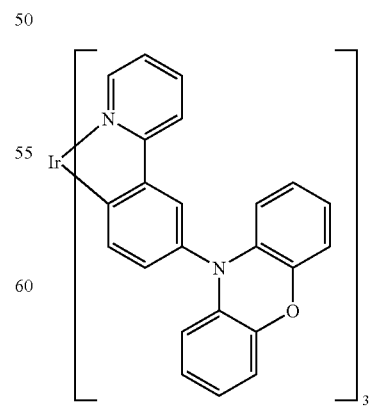

-continued
Example 16
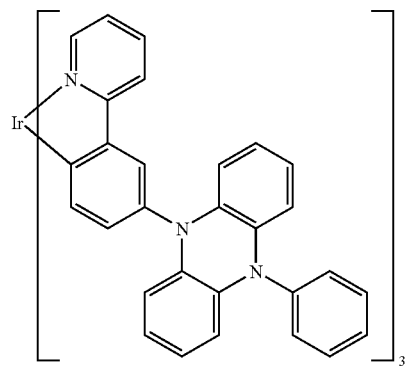
Example 17
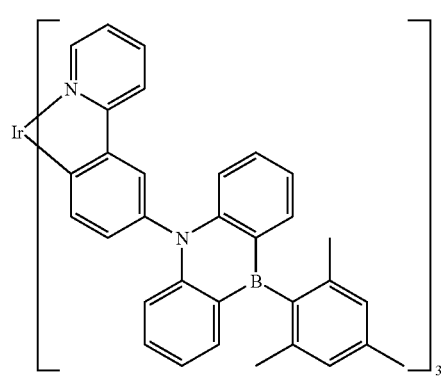
Example 18
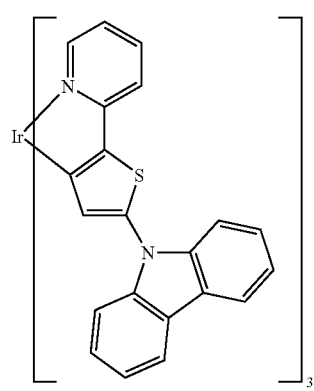
-continued
Example 19
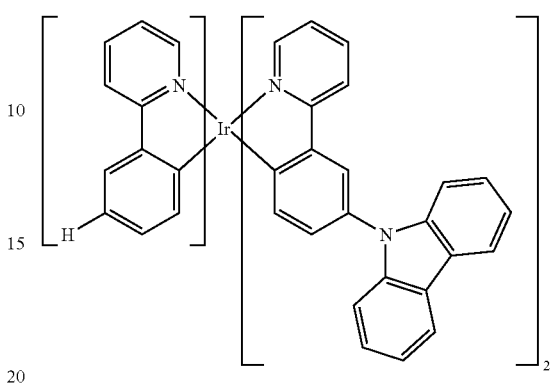
Example 20
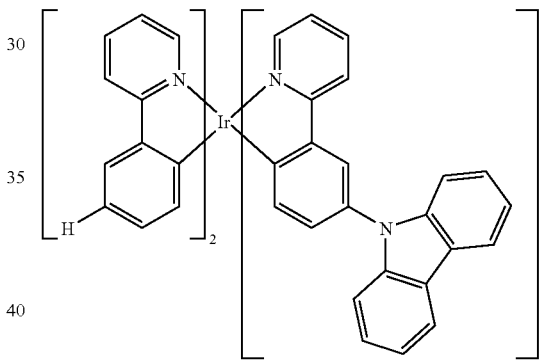
Example 21
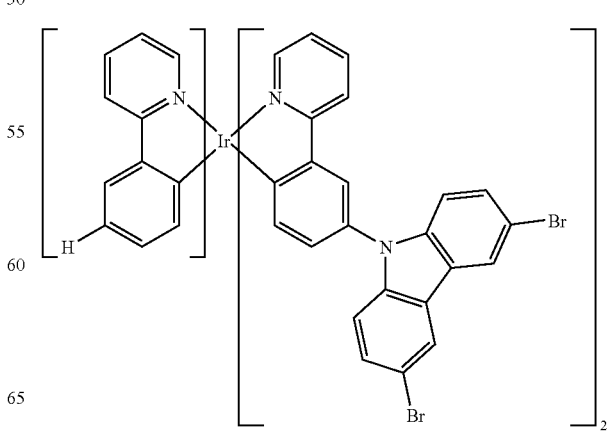

-continued

Example 22

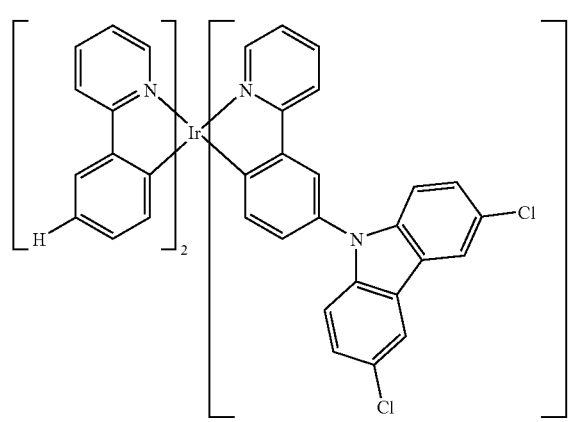

Example 23

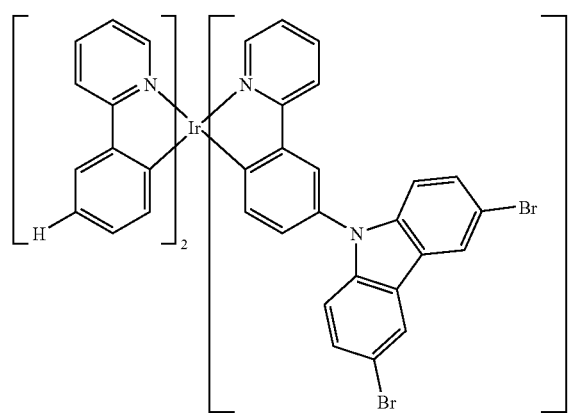

Example 24

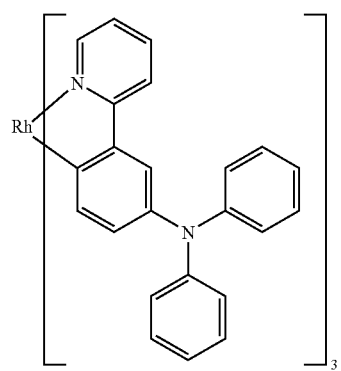

-continued

Example 25

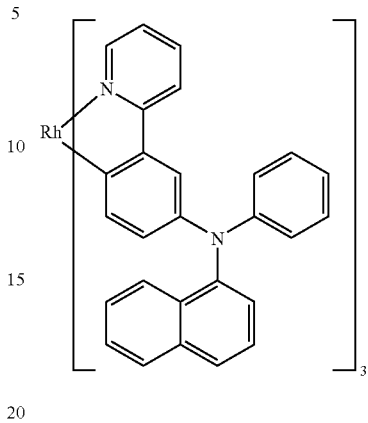

Example 26

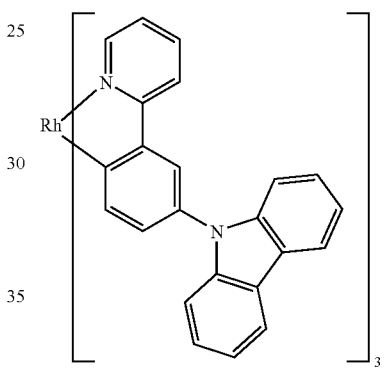

Example 27

The compounds according to the invention obtained in this way, for example compound according to Examples 13, 22, 23 and 24, can then be copolymerized as comonomers in conjugated or else semiconjugated polymers. They can also be incorporated by polymerization, inter alia, into soluble polyfluorenes (for example according to EP-A-842208 or WO 00/22026), poly-spiro-bifluorenes (for example according to EP-A-707020), poly-para-phenylenes (for example WO 92/18552), polycarbazoles, polythiophenes (for example according to EP-A-1028136) or else copolymers which contain a plurality of the units mentioned here.

These polymers find use as active components in electronic components, for example organic light-emitting diodes (OLEDs), organic integrated circuits (O-ICs), organic field-effect transistors (OFETs), organic thin-film transistors (OTFTs), organic solar cells (O-SCs) or else organic laser diodes (O-lasers).

The polyfluorenes disclosed in EP-A-842208 and WO 00/22026 form part of this description.

The poly-spiro-bifluorenes disclosed in EP-A-707020 form part of this description.

The poly-para-phenylenes disclosed in WO 92/18552 form part of this description.

The polythiophenes disclosed in EP-A-1028136 form part of this description.

In addition, the compounds according to the invention can of course also be further functionalized, for example, by the abovementioned reaction types, and thus be converted to extended low molecular weight Rh or Ir complexes. An example to be mentioned here is the functionalization with arylboronic acids according to SUZUKI or with amines according to HARTWIG-BUCHWALD.

The present invention is illustrated in detail by the examples which follow, without wishing to restrict it thereto. Those skilled in the art can prepare further complexes according to the invention or apply the process according to the invention from the explanations without any inventive activity.

1. Synthesis of Symmetrically and Asymmetrically Functionalized Tris-Ortho-Metalated Organorhodium or Organoiridium Compounds:

The syntheses which follow were, unless stated otherwise, carried out under a protective gas atmosphere in dried solvent. The reactants were obtained from ALDRICH [diphenylamine, phenyl-1-naphthylamine, carbazole, sodium tert-butoxide, anhydrous potassium phosphate, pailadium(II) acetate, tri-tert-butylphosphine]. fac-Tris[2-(2-pyridinyl-κN)(5-bromophenyl)-κC]-iridium(III) was prepared as described in the unpublished application DE 10109027.7.

The assignment of the $^{13}C\{^1H\}$ NMR signals was in each case confirmed by DEPT-135 spectra (p=primary, t=tertiary, q=quaternary carbon atom).

EXAMPLE 1 fac-Tris[2-(2-pyridinyl-κN)(5-(N-carbazolyl)phenyl)-κC]-iridium(III)

A mixture of 8.915 g (10 mmol) of fac-tris[2-(2-pyridinyl-κN)(5-bromophenyl)-κC]-iridium(III), 10.033 g (60 mmol) of carbazole, 25.474 g (120 mmol) of tripotassium phosphate (anhydrous), 134.7 mg (0.6 mmol) of palladium(II) acetate, 607.0 mg (3 mmol) of tri-tert-butylphosphine, 200 g of glass beads (diameter 0.6 cm) and 200 ml of xylene (isomer mixture) was heated to 130° C. for 60 h with good stirring by a precision glass stirrer. After cooling, the glass beads were sieved off. The filtrate was washed twice with 200 ml of water each time. Subsequently, the microcrystalline precipitate was filtered off (P4). The microcrystalline precipitate was dissolved in 500 ml of chloroform, and the solution was filtered off through Celite, concentrated to a volume of 50 ml and finally admixed with stirring with 400 ml of ethanol. The yellow, microcrystalline precipitate obtained in this way was filtered off (P4) and washed three times with 100 ml of ethanol each time and then dried under reduced pressure (60° C., $10^{-4}$ mbar). The yield, at a purity of >99.0% by $^1$H NMR, was 10.838–11.140 g, corresponding to 94.2–96.8%.

$^1$H NMR (CDCl$_3$, 50 µl of N$_2$H$_4$.H$_2$O): [ppm]=8.13–8.09 (br. m, 6H), 7.82–7.77 (br. m, 6H), 7.69–7.67 (br. m, 3H), 7.62–7.58 (m, 3H), 7.41–7.37 (br. m, 6H), 7.34–7.29 (br. m, 6H), 7.25–7.19 (m, 9H), 7.14–7.11 (m, 3H), 7.02–6.98 (m, 3H). $^{13}C\{^1H\}$ NMR (CDCl$_3$, 50 µl of N$_2$H$_4$.H$_2$O): [ppm]=166.01 (q), 160.06 (q) 147.35 (q), 145.16 (q), 141.51 (q), 138.11 (t), 136.64 (t), 130.41 (t), 129.32 (t), 125.68 (t), 123.05 (q), 122.95 (t), 122.71 (t), 120.17 (t), 119.40 (t), 119.35 (t), 110.08 (t).

EXAMPLE 2 fac-Tris[2-(2-pyridinyl-κN)(5-(N-carbazolyl)phenyl)-κC]-iridium(III)

Procedure similar to Example 1, except replacing fac-tris[2-(2-pyridinyl-κN)(5-bromophenyl)-κC]-iridium(III) with 10.325 g (10 mmol) of fac-tris[2-(2-pyridinyl-κN)(5-iodophenyl)-κC]-iridium(III).

The yield, at a purity of >99.0% by $^1$H NMR, was 10.943–11.162 g, corresponding to 95.1–97.0%.

$^1$H and $^{13}C\{^1H\}$ NMR spectra see Example 1.

EXAMPLE 3 fac-Tris[2-(2-pyridinyl-κN)(5-(N-diphenylamino)phenyl)κC]-iridium(III)

A mixture of 8.915 g (10 mmol) of fac-tris[2-(2-pyridinyl-κN)(5-bromophenyl)-κC]-iridium(III), 6.769 g (40 mmol) of diphenylamine, 4.806 g (50 mmol) of sodium tert-butoxide, 22.5 mg (0.1 mmol) of palladium(II) acetate, 40.5 mg (0.2 mmol) of tri-tert-butylphosphine and 200 ml of toluene was heated to reflux for 16 h with good stirring by a precision glass stirrer. The cooled reaction mixture was washed twice with 200 ml of water each time. Subsequently, the microcrystalline precipitate was filtered off (P4). The microcrystalline precipitate was dissolved in 500 ml of chloroform, and the solution was filtered through Celite, concentrated to a volume of 50 ml and finally admixed with stirring with 400 ml of ethanol. The orange, microcrystalline precipitate obtained in this way was filtered off (P4) and washed three times with 100 ml of ethanol each time and then dried under reduced pressure (60° C., $10^{-4}$ mbar). The yield, at a purity of >99.0% by $^1$H NMR, was 11.022–11.290 g, corresponding to 95.3–97.6%.

$^1$H NMR (CDCl$_3$, 50 µl of N$_2$H$_4$.H$_2$O): [ppm]=7.70–7.67 (br. m, 3H), 7.56–7.51 (m, 6H), 7.46–7.44 (m, 3H), 7.17–7.12 (m, 12H), 7.05–7.02 (m, 12H), 6.89–6.84 (m, 12H), 6.73–6.71 (m, 3H). $^{13}C\{^1H\}$ NMR (CDCl$_3$, 50 µl of N$_2$H$_4$.H$_2$O): [ppm]=166.30 (q), 156.65 (q) 148.32 (q), 147.11 (t), 144.64 (q), 140.09 (q), 137.66 (t), 135.90 (t), 129.21 (t), 128.89 (t), 122.54 (t), 122.46 (t), 121.96 (t), 121.13 (t), 119.22 (t).

EXAMPLE 4 fac-Tris[2-(2-pyridinyl-κN)(5-(N-(1-naphthyl)phenyl)phenyl))-κC]-iridium(III)

A mixture of 8.915 g (10 mmol) of fac-tris[2-(2-pyridinyl-κN)(5-bromophenyl)-κC]-iridium(III), 8.772 g (40 mmol) of N-(1-naphthyl)phenylamine, 4.806 g (50 mmol) of sodium tert-butoxide, 22.5 mg (0.1 mmol) of palladium(II) acetate, 40.5 mg (0.2 mmol) of tri-tert-butylphosphine and 200 ml of toluene was heated to reflux for 12 h with good stirring by a precision glass stirrer. The cooled reaction mixture was washed twice with 200 ml of water each time. Subsequently, the microcrystalline precipitate was filtered off (P4). The microcrystalline precipitate was dissolved in 500 ml of chloroform, and the solution was filtered through Celite, concentrated to a volume of 50 ml and finally admixed with stirring with 400 ml of ethanol. The microcrystalline precipitate obtained in this way was filtered off (P4) and washed three times with 100 ml of ethanol each time and then dried under reduced pressure (60° C., $10^{-4}$ mbar). The yield, at a purity of >99.0% by $^1$H NMR, was 12.417–12.683 g, corresponding to 95.0–96.8%.

$^1$H NMR (CD$_2$Cl$_2$, 50 µl of N$_2$H$_4$.H$_2$O): [ppm]=7.99–7.95 (m, 3H), 7.84–7.80 (m, 3H), 7.70–7.67 (m, 3H), 7.61–7.56 (m, 3H), 7.56–7.53 (m, 3H), 7.53–7.45 (m, 6H), 7.43–7.32 (m, 6H), 7.32–7.24 (m, 6H), 7.06–7.01 (m, 6H), 6.87–6.83 (m, 3H), 6.77–6.70 (m, 12H), 6.68–6.65 (m, 3H). $^{13}C\{^1H\}$ NMR (CD$_2$Cl$_2$, 50 μl of N$_2$H$_4$.H$_2$O): [ppm] =166.36 (q) 155.68 (q) 149.98 (q), 147.48 (t), 144.87 (q), 144.29 (q), 141.44 (q), 141.44 (q), 137.51 (t), 136.38 (t), 135.64 (q), 131.58 (q), 129.03 (t), 128.54 (t), 127.56 (t), 127.01 (t), 126.64 (t), 126.20 (t), 126.20 (t), 126.02 (t), 124.77 (t), 122.55 (t), 120.89 (t), 119.58 (t), 119.34 (t), 119.18 (t).

EXAMPLE 5 fac-Tris[2-(2-pyridinyl-N)(5-(bis(4-methoxyphenyl)phenyl))-κC]-iridium(III)

A mixture of 8.915 g (10 mmol) of fac-tris[2-(2-pyridinyl-κN)(5-bromophenyl)-κC]-iridium(III), 9.171 g (40 mmol) of bis(4-methoxyphenyl)amine, 4.806 g (50 mmol) of sodium tert-butoxide, 22.5 mg (0.1 mmol) of palladium(II) acetate, 40.5 mg (0.2 mmol) of tri-tert-butylphosphine and 200 ml of toluene was heated to reflux for 12 h with good stirring by a precision glass stirrer. The cooled reaction mixture was washed twice with 200 ml of water each time. Subsequently, the microcrystalline precipitate was filtered off (P4). The microcrystalline precipitate was dissolved in 500 ml of chloroform, and the solution was filtered through Celite, concentrated to a volume of 50 ml and finally admixed with stirring with 400 ml of ethanol. The microcrystalline precipitate obtained in this way was filtered off (P4) and washed three times with 100 ml of ethanol each time and then dried under reduced pressure (60° C., 10$^{-4}$ mbar). The yield, at a purity of >99.0% by $^1$H NMR, was 12.763–12.994 g, corresponding to 94.6–96.3%.

$^1$H NMR (CDCl$_3$, 50 μl of N$_2$H$_4$.H$_2$O): [ppm]=7.58–7.55 (m, 3H), 7.47–7.41 (m, 6H), 7.29–7.27 (m, 3H), 6.90–6.85 (m, 12H), 6.79–6.75 (m, 3H), 6.72–6.69 (m, 3H), 6.68–6.63 (m, 12H), 6.60–6.57 (m, 3H), 3.73 (s, 18H, CH$_3$). $^{13}C\{^1H\}$ NMR (CDCl$_3$, 50 μl of N$_2$H$_4$.H$_2$O): [ppm]=166.45 (q), 154.73 (q), 154.33 (q), 147.06 (t), 144.19 (t), 142.37 (q), 141.18 (q), 137.30 (t), 135.67 (t), 127.27 (t), 124.29 (t), 121.77 (t), 120.28 (t), 119.01 (t), 114.34 (t), 55.47 (p).

What is claimed is:

1. A compound of the formula (I) or (II)

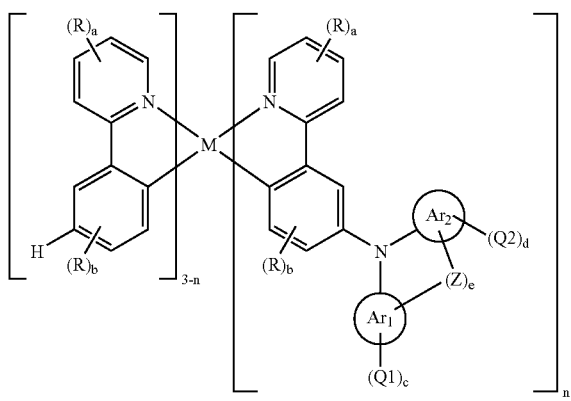

compounds (I)

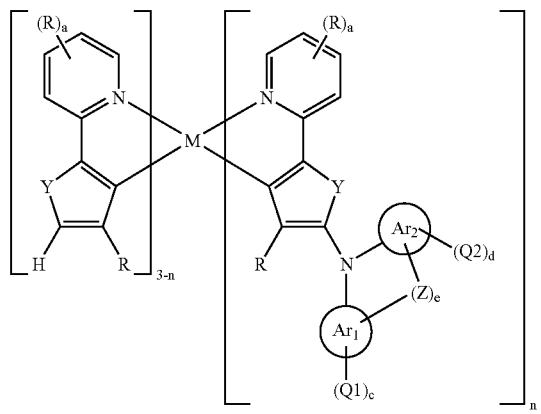

compounds (II)

where the symbols and indices are defined as follows:

M is Rh or Ir;

Y is O, S or Se;

Z is B—R$^1$, C(R)$_2$, —CH=CH—, —CR$^1$=CH—, —CR$^1$=CR$^1$—, C=O, NH, NR$^1$, PR$^1$, P(O)R$^1$, P(S)R$^1$, O, S, S=O, S(=O)$_2$, Se or a C—C single bond;

R is the same or different at each occurrence and is H, F, Cl, NO$_2$, CN, a straight-chain or branched or cyclic alkyl or alkoxy group which has from 1 to 20 carbon atoms and in which one or more nonadjacent CH$_2$ groups is optionally replaced by —O—, —S—, —NR$^1$— or —CONR$^2$—, and In which one or more hydrogen atoms is optionally replaced by F, or an aryl or heteroaryl group having from 4 to 14 carbon atoms which is optionally substituted by one or more nonaromatic R radicals; and a plurality of R substituents, either on the same ring or on the two different rings together form a further mono- or polycyclic ring system;

Ar$_1$ and Ar$_2$ are the same or different and are each an aryl or heteroaryl group having from 1 to 40 carbon atoms;

Q1 and Q2 are the same or different at each occurrence and are each F, Cl, Br, CN, NO$_2$ or a straight-chain or branched or cyclic alkyl or alkoxy group which has from 1 to 20 carbon atoms and in which one or more nonadjacent CH$^2$ groups is optionally replaced by —O—, —S—, —CO—, —COO—, —O—CO—, —NR$^1$—, —(NR$^2$R$^3$)$^+$A$^-$ or —CONR$^4$, and in which one or more hydrogen atoms is optionally replaced by F, or an aryl or heteroaryl group having from 4 to 14 carbon atoms which is optionally substituted by one or more nonaromatic R radicals;

A$^-$ is a singly charged anion;

R$^1$, R$^2$, R$^3$ and R$^4$ are the same or different and are each H or an aliphatic or aromatic hydrocarbon radical having from 1 to 20 carbon atoms;

a is 0, 1, 2, 3 or 4;

b is 0, 1, 2 or 3;

c and d are each 0, 1, 2, 3, 4 or 5;

e is 0 or 1;

n is 1, 2 or 3.

2. The compound as claimed in claim 1, wherein a is 0 or 1;

b is 0 or 1; and c and d are each 0 or 1.

3. The compound as claimed in claim 1, wherein the compound is of the formula (Ia) or (IIa)

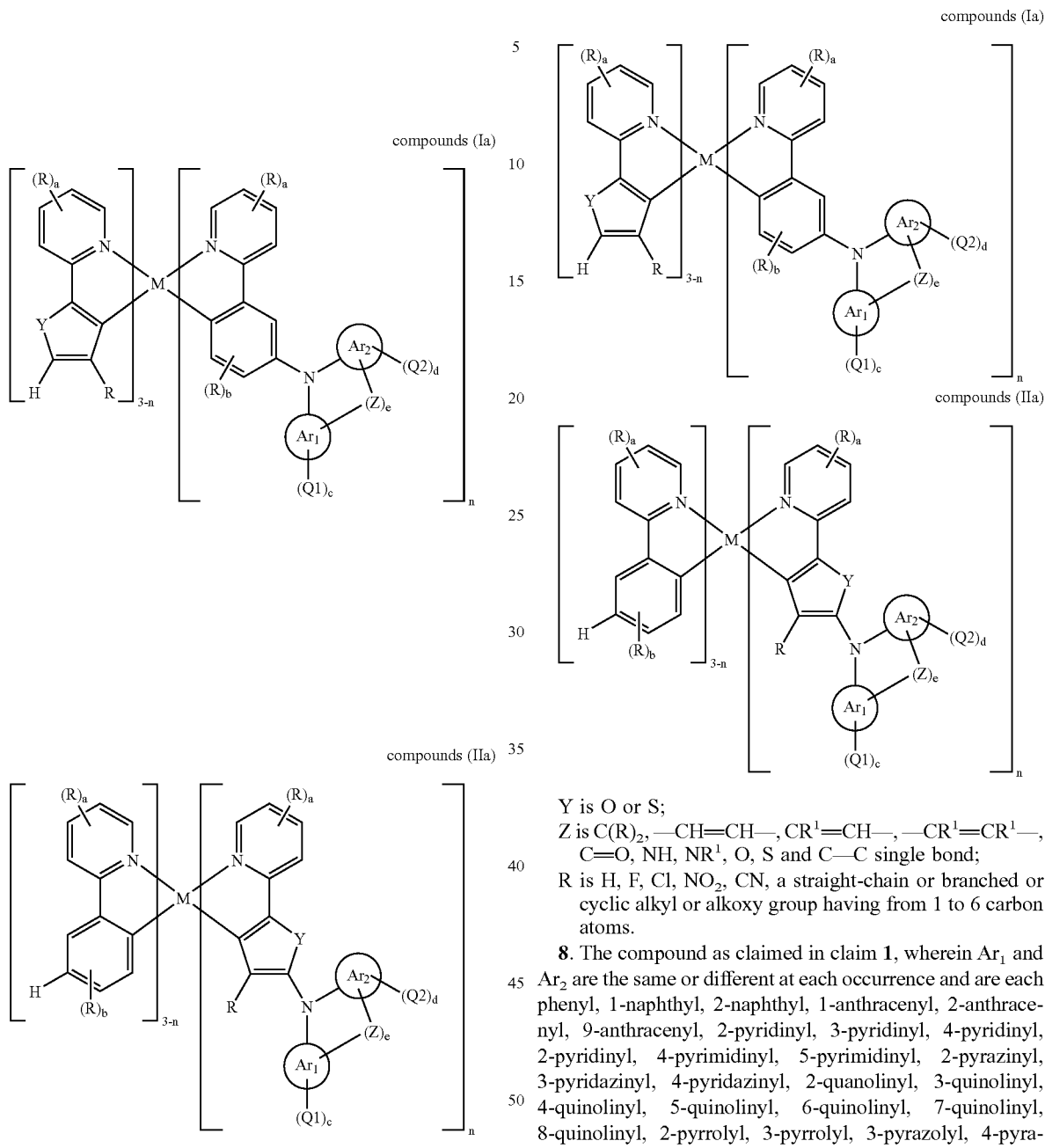

where the symbols and indices are as defined in claim 1.

4. The compound as claimed in claim 1 wherein Y is O or S.

5. The compound as claimed in claim 1, wherein Z is $C(R)_2$, —CH=CH—, —$CR^1$=CH—, —$CR^1$=$CR^1$—, C=O, NH, $NR^1$, O, S and C—C single bond.

6. The compound as claimed in claim 1, wherein R is H, F, Cl, $NO_2$, CN, a straight-chain or branched or cyclic alkyl or alkoxy group baying from 1 to 6 carbon atoms.

7. The compound as claimed in claim 3, wherein the compound is of the formula (Ia) or (IIa)

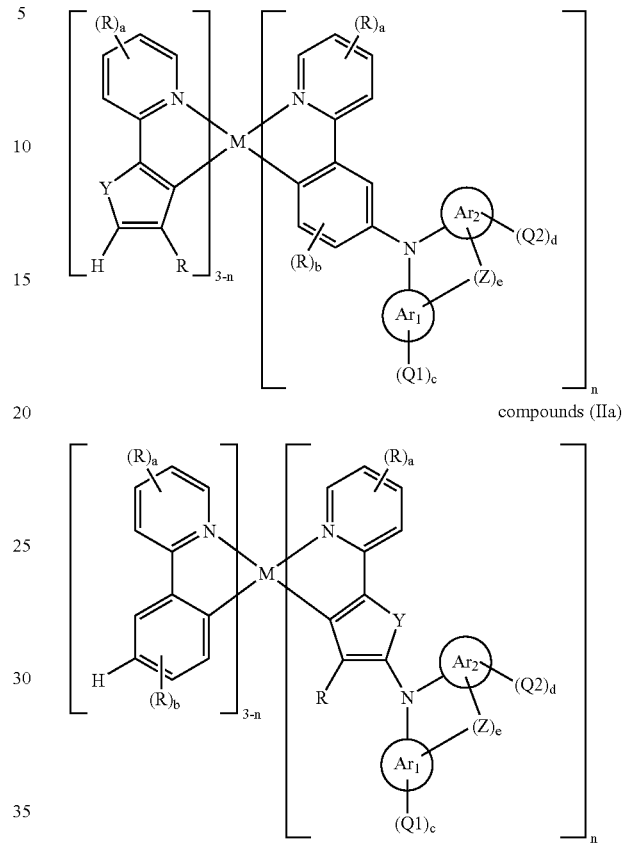

Y is O or S;
Z is $C(R)_2$, —CH=CH—, —$CR^1$=CH—, —$CR^1$=$CR^1$—, C=O, NH, $NR^1$, O, S and C—C single bond;
R is H, F, Cl, $NO_2$, CN, a straight-chain or branched or cyclic alkyl or alkoxy group having from 1 to 6 carbon atoms.

8. The compound as claimed in claim 1, wherein $Ar_1$ and $Ar_2$ are the same or different at each occurrence and are each phenyl, 1-naphthyl, 2-naphthyl, 1-anthracenyl, 2-anthracenyl, 9-anthracenyl, 2-pyridinyl, 3-pyridinyl, 4-pyridinyl, 2-pyrimidinyl, 4-pyrimidinyl, 5-pyrimidinyl, 2-pyrazinyl, 3-pyridazinyl, 4-pyridazinyl, 2-quanolinyl, 3-quinolinyl, 4-quinolinyl, 5-quinolinyl, 6-quinolinyl, 7-quinolinyl, 8-quinolinyl, 2-pyrrolyl, 3-pyrrolyl, 3-pyrazolyl, 4-pyrazolyl, 5-pyrazolyl, 2-imidazolyl, 4-imidazolyl, 5-imidazolyl, 2-thiophenyl, 3-thiophenyl, 2-selenophenyl, 3-selenophenyl, 2-furanyl, 3-furanyl or 2-(1,3,4-oxadiazol)yl.

9. The compound as claimed in claim 7, wherein $Ar_1$ and $Ar_2$ are the same or different at each occurrence and are each phenyl, 1-naphthyl, 2-naphthyl, 1-anthracenyl, 2-anthracenyl, 9-anthracenyl, 2-pyridinyl, 3-pyridinyl, 4-pyridinyl, 2-pyrimidinyl, 4-pyrimidinyl, 5-pyrimidinyl, 2-pyrazinyl, 3-pyridazinyl, 4-pyridazinyl, 2-quinolinyl, 3-quinolinyl, 4-quinolinyl, 5-quinolinyl, 6-quinolinyl, 7-quinolinyl, 8-quinolinyl, 2-pyrrolyl, 3-pyrrolyl, 3-pyrazolyl, 4-pyrazolyl, 5-pyrazolyl, 2-imidazolyl, 4-imidazolyl, 5-imidazolyl, 2-thiophenyl, 3-thiophenyl, 2-selenophenyl, 3-selenophenyl, 2-furanyl, 3-furanyl or 2-(1,3,4-oxadiazol)yl.

10. The compound as claimed in claim 1, wherein the diarylamino unit Ar$_1$—N—Ar$_2$ is a diphenylamino, an N-(1-naphthyl)phenylamino, a di(1-naphthyl) amino, an N-(2-naphthyl)phenylamino, a di(2-naphthyl)amino, a bis(4-methoxyphenyl) amino, a bis(4-dimethylaminophenyl) amino, a carbazolyl, a 3,6-dichlorocarbazolyl, a 3,6-dibromocarbazolyl, a phenoxazine or a phenothiazine unit.

11. The compound as claimed in claim 9, wherein the diarylamino unit Ar$_1$—N—Ar$_2$ is a diphenylamino, an N-(1-naphthyl)phenylamino, a di(1-naphthyl) amino, an N-(2-naphthyl)phenylamino, a di(2-naphthyl)amino, a bis(4-methoxyphenyl) amino, a bis(4-dimethylaminophenyl) amino, a carbazolyl, a 3,6-dichlorocarbazolyl, a 3,6-dibromocarbazolyl, a phenoxazine or a phenothiazine unit.

12. The compound as claimed in claim 1, wherein Q1 and Q2 are each F, Cl, Br, CN, NO$_2$ or a straight-chain or branched or cyclic alkyl or alkoxy group which has from 1 to 6 carbon atoms and in which one CH$_2$ group is optionally replaced by
—NR$^1$—.

13. The compound as claimed in claim 11, wherein Q1 and Q2 are each F, Cl, Br, CN, NO2 or a straight—chain or branched or cyclic ailcyl or alkoxy group which has from 1 to 6 carbon atoms and in which one CH$_2$ group is optionally replaced by
—NR$^1$—.

14. The process for preparing the compounds as claimed in claim 1, which comprises reacting the compounds (III) and (IV)

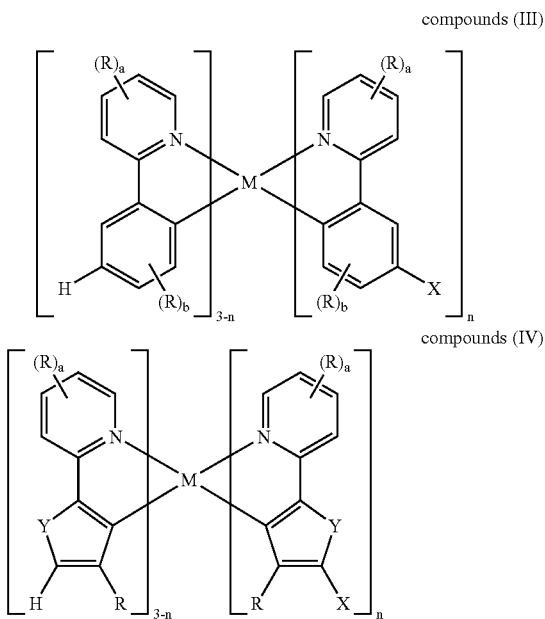

compounds (III)

compounds (IV)

where
X is Cl, Br or I
with a secondary diarylamine of the formula (I)

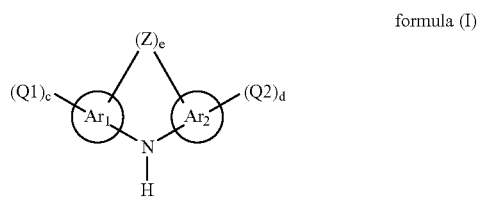

formula (I)

and the remaining symbols and indices are as defined in claim 1 in a reaction medium and in the presence of a transition metal or of a transition metal compound, or of a phosphorus or nitrogen additive and of a base.

15. The process as claimed in claim 14, wherein the transition metal or transition metal compound used is nickel or nickel compounds or palladium or palladium compounds.

16. The process as claimed in claim 15, wherein the molar ratio of nickel or of a nickel compound, or of palladium or of a palladium compound to the compounds (III) and (IV) is from 0.1 n:1 to 0.00001n:1.

17. The process as claimed in claim 14, wherein the phosphorus additive used is a phosphine.

18. The process as claimed in claim 14, wherein the nitrogen additive used is an imidazolium salt; imidazol-2-ylidene, amine or amino carboxylic acid.

19. The process as claimed in claim 16, wherein the nitrogen additive used is an imidazolium salt, imidazol-2-ylidene, amine or amino carboxylic acid and the phosphorous additive used is phosphine.

20. The process as claimed in claim 15, wherein the molar ratio of the phosphorus or nitrogen additives to the transition metals or transition metal compounds nickel and nickel compounds, palladium or palladium compounds is from 0.5:1 to 1000:1.

21. The process as claimed in claim 14, wherein the molar ratio of the organic or inorganic base to the compounds (III) or (IV) is from 0.5n:1 to 100n:1.

22. The compound as claimed in claim 1, wherein its purity (determined by means of 1H NMR and/or HPLC) is more than 99%.

* * * * *

UNITED STATES PATENT AND TRADEMARK OFFICE
CERTIFICATE OF CORRECTION

PATENT NO. : 7,094,897 B2
APPLICATION NO. : 10/474090
DATED : August 22, 2006
INVENTOR(S) : Philipp Stossel et al.

It is certified that error appears in the above-identified patent and that said Letters Patent is hereby corrected as shown below:

On the Title Page:

Item (75), Inventors, "Phillip Stossel, Frankfurt (DE); Hubert Spreitzer, Viernheim (DE); Heinrich Becker, Glashütten (DE)" should read -- Phillip Stossel, Frankfurt (DE); Hubert Spreitzer, Viernheim (DE); Heinrich Becker, Niederjosbach (DE)--

Item (86), § 371 (c)(1), (2),(4) Date, "Feb. 19, 2004" should read -- Oct. 28, 2003 --

In the Claims:

Column 24, line 67, "c andd are each 0 or 1." should read -- c and d are each 0 or 1.--

Column 26, line 48, "2-pyridinyl, 4-pyrimidinyl, 5-pyrimidinyl, 2-pyrazinyl" should read -- 2-pyrimidinyl, 4-pyrimidinyl, 5-pyrimidinyl, 2-pyrazinyl --

Column 26, line 49, "3-pyridazinyl, 4-pyridazinyl, 2-quanolinyl, 3-quinolinyl" should read -- 3-pyridazinyl, 4-pyridazinyl, 2-quinolinyl, 3-quinolinyl --

Column 28, line 30, "from 0.1 n:1 to 0.00001n:1." should read -- from 0.1n:1 to 0.00001n:1. --

Signed and Sealed this

Twenty-third Day of January, 2007

JON W. DUDAS
*Director of the United States Patent and Trademark Office*